United States Patent
Nakamura et al.

[11] Patent Number: 6,045,104
[45] Date of Patent: Apr. 4, 2000

[54] MEDICAL STAND APPARATUS

[75] Inventors: Katsushige Nakamura; Masao Doi; Masakazu Nakamura, all of Tokyo, Japan

[73] Assignee: Mitaka Kohki Co., Ltd., Tokyo, Japan

[21] Appl. No.: 09/049,710

[22] Filed: Mar. 27, 1998

[30] Foreign Application Priority Data

Mar. 31, 1997 [JP] Japan ..................... 9-080176
Jul. 11, 1997 [JP] Japan ..................... 9-186961

[51] Int. Cl.⁷ ............................................. E04G 3/00
[52] U.S. Cl. ........................ 248/280.11; 248/123.11; 248/123.2
[58] Field of Search ...................... 248/276.1, 280.11, 248/281.11, 282.1, 284.1, 123.11, 123.2, 124.1, 292.11, 580, 591, 593

[56] References Cited

U.S. PATENT DOCUMENTS

| | | | |
|---|---|---|---|
| 2,470,284 | 5/1949 | Bergmans et al. | 248/280.11 |
| 3,396,931 | 8/1968 | Eckstein | 248/280.11 |
| 3,883,105 | 5/1975 | Matsumoto | 248/281 |
| 4,241,891 | 12/1980 | Rudolph | 248/123.1 |
| 4,364,535 | 12/1982 | Itoh et al. | 248/123.1 |
| 5,192,963 | 3/1993 | Hill | 354/81 |
| 5,415,057 | 5/1995 | Nihei et al. | 74/490.01 |
| 5,609,316 | 3/1997 | Tigliev | 248/123.11 |
| 5,651,718 | 7/1997 | Nakamura | 248/123.2 |
| 5,687,943 | 11/1997 | Campbell | 248/331 |
| 5,697,757 | 12/1997 | Lindsay | 248/280.11 X |
| 5,713,545 | 2/1998 | Nakamura | 248/123.2 |

Primary Examiner—Ramon O. Ramirez
Assistant Examiner—Tan Le
Attorney, Agent, or Firm—Jordan and Hamburg LLP

[57] ABSTRACT

A medical stand apparatus includes a drive mechanism for moving a counterweight in a balancing direction and a balance-sensing mechanism for sensing balancing-state of a parallel link mechanism and for sending a signal to the drive mechanism. The balance-sensing mechanism is provided on a connection shaft on which arms of the parallel link mechanism intersect with each other. When the angle between the arms on the connection shaft is displaced due to upset of balance, a switch corresponding to the direction of angular displacement is pressed by the tip portion of a lock pin. As a result, the pressed switch sends a signal to the drive mechanism, whereby the counterweight is automatically moved in a balancing direction. Since balancing adjustment can be automatically performed in this manner, time required for the balancing-adjustment work is reduced, and a person unfamiliar with the balancing-adjustment work can readily carry out the work.

6 Claims, 9 Drawing Sheets

$G_1 \times L_4 = G_2 \times L_3$

MEDICAL STAND APPARATUS

BACKGROUND OF THE INVENTION

1. Field of the Invention

The present invention relates to a medical stand apparatus capable of holding a medical optical device motionless in a desired spatial position.

2. Description of the Related Art

Cerebral surgery and cardiosurgery include a so-called microsurgery, in which a doctor performs a surgical operation while observing an affected part through an operation microscope serving as a "medical optical device." For use in such microsurgery, there have been proposed various stand apparatuses that can hold a heavy operation microscope and its attachment in a desired spatial position (for example, in Japanese Patent Application Laid-Open (kokai) No. 6-269463). A stand apparatus of this kind is generally composed of a parallel link mechanism which is composed of a plurality of arms. The parallel link mechanism is supported at a predetermined swing pivot. An operation microscope and/or its attachment is held at one end of the parallel link mechanism, and a counterweight is provided at the other end of the parallel link mechanism so as to counterbalance with the operation microscope and/or its attachment. That is, the parallel link mechanism has a balancing structure.

Such a balance-type stand apparatus is installed at a site selected as being optimum for a surgical operation concerned within an operating room, and undergoes balancing adjustment at the site. Since an attachment, such as a side viewer for use by an assistant doctor, a video camera, and the like, are attached to an operation microscope, the position of a counterweight is manually adjusted in accordance with the total weight of the operation microscope and the attachments so as to establish the overall balance of the apparatus.

However, according to such conventional technology, balancing adjustment requires relatively long time, since the position of the counterweight is manually adjusted. Also, when such a stand apparatus is in an imbalanced state, a parallel link mechanism moves to a large extent; thus, there is involved a danger that part of the parallel link may hit a person who is present near the apparatus.

Also, since an operation microscope is located at the side of its supporting device, a sufficient amount of free space is not available around the operation microscope. As a result, movement of the head of a doctor around the operation microscope is limited.

SUMMARY OF THE INVENTION

The present invention has been accomplished in view of such conventional technology, and an object of the invention is to provide a medical stand apparatus in which balancing adjustment can be automatically carried out within a short time and in which a parallel mechanism does not move to a large extent when balance is upset.

Another object of the present invention is to provide a balancing support mechanism for an operation microscope which is less likely to limit the movement of the head of a doctor around the operation microscope.

To achieve the above objects, the present invention provides a medical stand apparatus in which a parallel link mechanism comprising a plurality of arms is supported at a predetermined swing pivot, a medical optical device and/or an attachment is held at one end of the parallel link mechanism, and a counterweight is provided at the other end of the parallel link mechanism so as to counterbalance with the medical optical device and/or the attachment. The medical stand apparatus comprises a drive mechanism for moving the counterweight in a balancing direction and a balance-sensing mechanism for sensing the state of balance of the parallel link mechanism and for sending a signal to the drive mechanism. The balance-sensing mechanism is provided on a connection shaft on which arms of the parallel link mechanism intersect with each other. The balance-sensing mechanism comprises a pair of stopper portions formed on one of the intersecting arms in a position corresponding to the connection shaft in such a manner as to face each other with a predetermined clearance formed between the stopper portions; a lock pin provided on the other arm such that the tip portion of the lock pin can be inserted into or removed from the clearance; and a pair of switches provided on the one arm such that a relevant switch is pressed by the tip portion of the lock pin when the angle between the arms changes.

Accordingly, when the angle between the arms on the connection shaft changes due to upset of balance, a switch corresponding to the direction of change in the angle is pressed by the tip portion of the lock pin. As a result, the pressed switch sends a signal to the drive mechanism, whereby the counterweight is automatically moved in a balancing direction. Since balancing adjustment can be automatically performed in this manner, time required for the balancing-adjustment work is reduced, and a person unfamiliar with the balancing-adjustment work can readily carry out the work. Once balance is automatically kept, even when the lock pin is removed from the clearance, the medical optical device and the like and the counterweight are sustained in the balanced state. Accordingly, even when the medical optical device and the like are moved to any spatial position, they stand motionless there.

Also, while the tip portion of the lock pin is inserted into the clearance, even when the arms of the parallel link mechanism attempt to turn to a large extent, the relevant stopper portion abuts the tip portion of the lock pin to thereby prevent the arms from further turning. Thus, there is not involved the danger that the parallel link mechanism moves to a large extent and hits a person present nearby. Since the turning movement of the parallel link mechanism is forcibly hindered through physical engagement between the stopper portions and the lock pin, even when an electrical failure occurs in the switches or the like, a large movement of the parallel link mechanism which would otherwise be induced by the imbalance of weight is completely hindered, thus providing an excellent degree of safety.

The present invention also provides a balancing support mechanism comprising: a center member supported at a tip of a stand apparatus in a manner rotatable about a vertical axis; a pair of parallel horizontal links which are supported in a turnable manner at upper and lower positions of the center member such that each horizontal link is supported at a position located lower than both end portions of the horizontal link; a pair of vertical links, each of which is supported in a turnable manner by the horizontal links at corresponding upper and lower end portions of the horizontal links; and a support link which is supported in a turnable manner at lower end portions of the vertical links and extends between the lower end portions of the vertical links in parallel with the horizontal links and which has a tilt shaft for supporting an operation microscope. The tilt shaft is located below a stationary point which stands stationary even when both end portions of the horizontal links move vertically. The combined center of gravity of the operation microscope and the support link balance with the combined center of gravity of the horizontal links and the vertical links in the direction in which the vertical links face each other with respect to the vertical axis.

Since the operation microscope is supported by the support link which is supported in a turnable manner at the lower end portions of the vertical links, the vertical links are not present around the operation microscope to thereby provide a sufficient amount of space around the operation microscope. Also, since the horizontal links are supported in a turnable manner on the center member at the positions located lower than corresponding end portions of the horizontal links, the stationary point is resultantly located below the lower end portions of the vertical links. If the combined center of gravity of the operation microscope and the support link is made coincide with the stationary point, balance is not kept, since the combined center of gravity of the horizontal links and the vertical links varies with respect to the stationary point. To avoid the problem, the combined center of gravity of the operation microscope and the support link is located below the stationary point to thereby keep balance. This enables the operation microscope to be located sufficiently below the lower end portions of the vertical links, thereby advantageously securing space around the operation microscope.

Preferably, the upper and lower horizontal links slide synchronously by the same length in the longitudinal direction of the horizontal links with respect to the center member. Accordingly, when the combined center of gravity of the operation microscope and the support link varies as a result of attachment of another device to the operation microscope, the horizontal links can be slid in a balancing direction so as to keep balance.

Preferably, the balancing support mechanism further comprises an imbalance sensor for sensing the imbalanced state between the combined center of gravity of the operation microscope and the support link and the combined center of gravity of the horizontal links and the vertical links, and a slide mechanism for synchronously sliding the upper and lower horizontal links to respective positions in accordance with a signal from the imbalance sensor such that balance is kept.

Thus, when the combined center of gravity of the operation microscope and the support link varies as a result of attachment of another device to the operation microscope, balancing adjustment is automatically performed by the imbalance sensor and the slide mechanism.

The above description should not be construed as limiting the present invention. The above and other objects, advantages, features, and applications of the present invention will become apparent from the following description given in conjunction with the accompanying drawings. Also, it is to be understood that modifications are possible without departing from the spirit of the invention and are encompassed in the scope of the invention.

DESCRIPTION OF THE PREFERRED EMBODIMENTS

Figure 1:
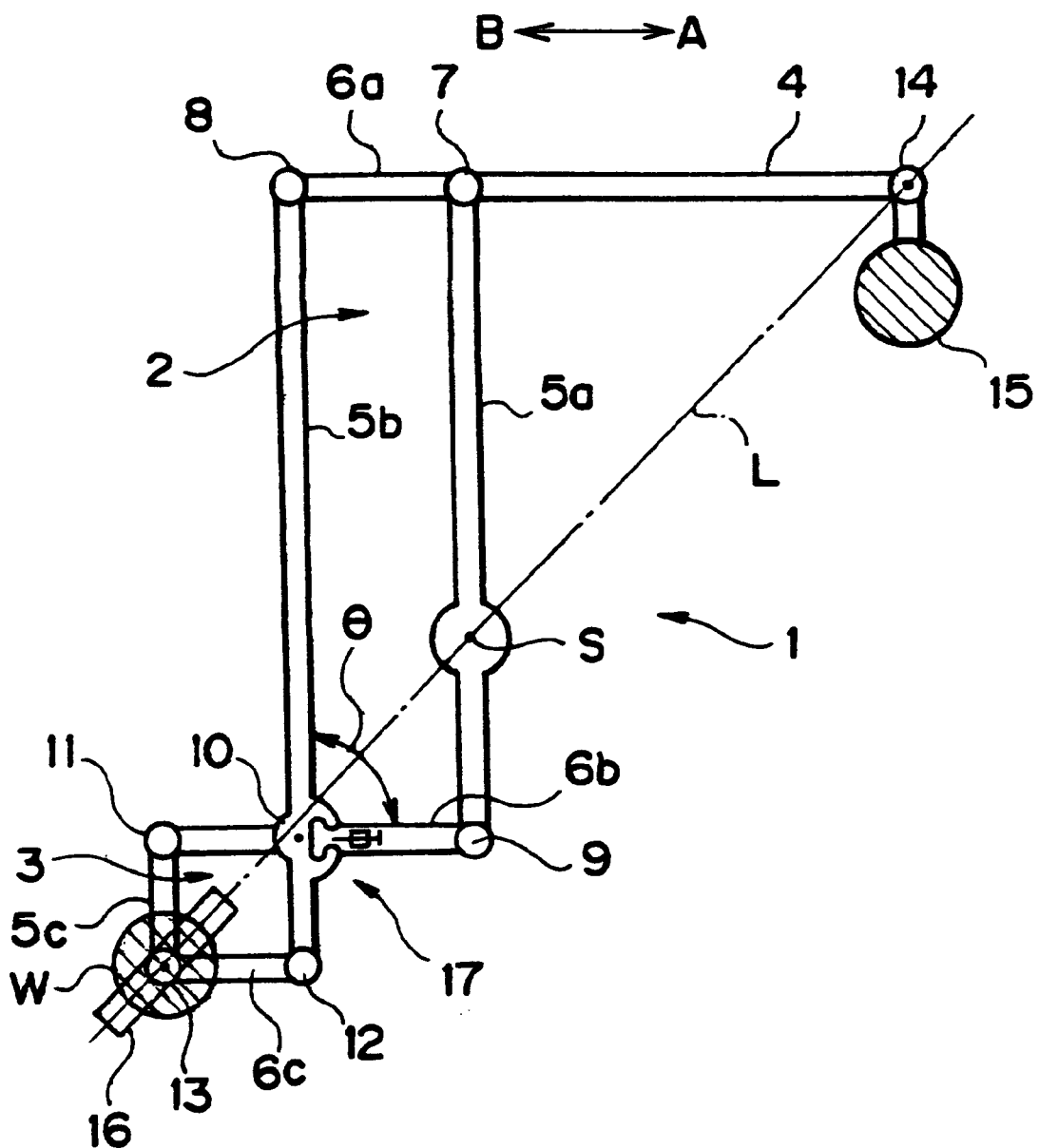
FIG. 1 is a schematic view showing a medical stand apparatus according to an embodiment of the present invention.

Embodiments of the present invention will now be described with reference to the drawings. In the drawings, symbol A denotes the front side, and symbol B denotes the rear side.

A parallel link mechanism 1 comprises a first parallel link 2, a second parallel link 3, and a support arm 4. The first parallel link 2 and the second parallel link 3 are formed through combination of three vertical arms 5a, 5b, and 5c and three horizontal arms 6a, 6b, and 6c. The vertical arms 5a, 5b, and 5c and the horizontal arms 6a, 6b, and 6c cross each other in a turnable manner via connection shafts 7 to 13.

The support arm 4 is formed by extending the upper horizontal arm 6a forward beyond the connection shaft 7. A swing pivot S is provided at an intermediate position of the front-side vertical arm 5a so as to support the entire parallel link mechanism 1 at the swing pivot S by means of an unillustrated mount. Each of the connection shafts 7 to 13 is provided with an electromagnetic clutch so as to lock or unlock the parallel link mechanism 1 by turning ON or OFF the electromagnetic clutches. The electromagnetic clutches are normally in the state of locking the parallel link mechanism 1 and unlock the parallel link mechanism 1 when the mechanism is to be used. Accordingly, the locked state is sustained even when a power failure occurs and also at the initial stage in which a stand apparatus is set.

An operation microscope 15 serving as a "medical optical device" is supported at a tip 14 of the support arm 4. A drive mechanism 16 is provided on the connection shaft 13 of the second parallel link 3. The drive mechanism 16 has a known structure which utilizes a threaded rod, a nut, and the like. A counterweight W is attached to the drive mechanism 16. The drive mechanism 16 is adapted to move the counterweight W along a straight line L connecting the tip 14 of the support arm 4, the swing pivot S, and the connection shaft 13.

For example, assuming that the counterweight W and the operation microscope 15 are completely balanced with each other in the state shown in FIG. 1 (the angle θ between the vertical arm 5b and the horizontal arm 6b is 90 degrees), even when the operation microscope 15 is moved vertically (or in a front-rear direction) from the state of FIG. 1, the operation microscope 15 stands motionless in a spatial destination point.

Figure 2:
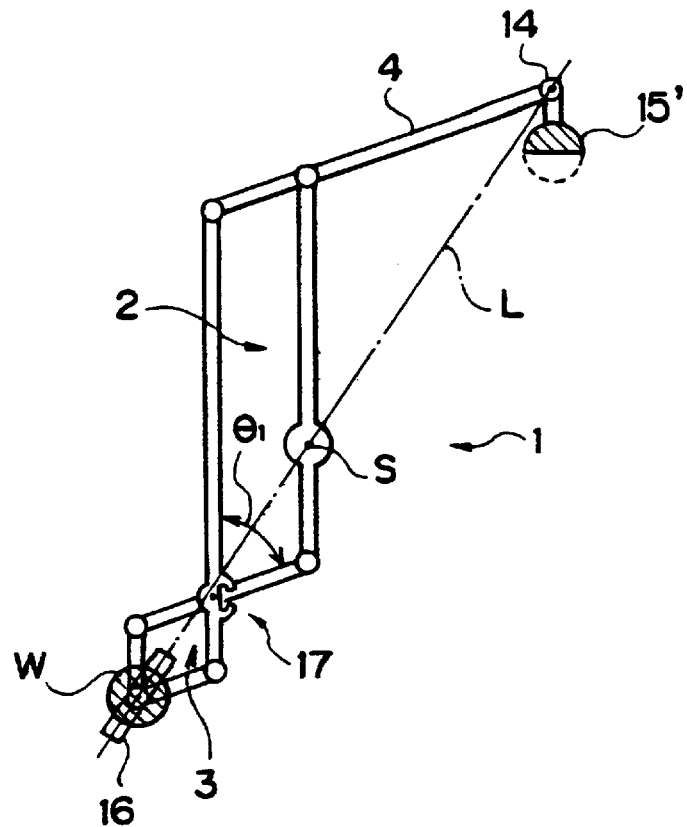
FIG. 2 is a schematic view corresponding to FIG. 1, showing a case in which an operation microscope is lighter than a counterweight.
Figure 3:
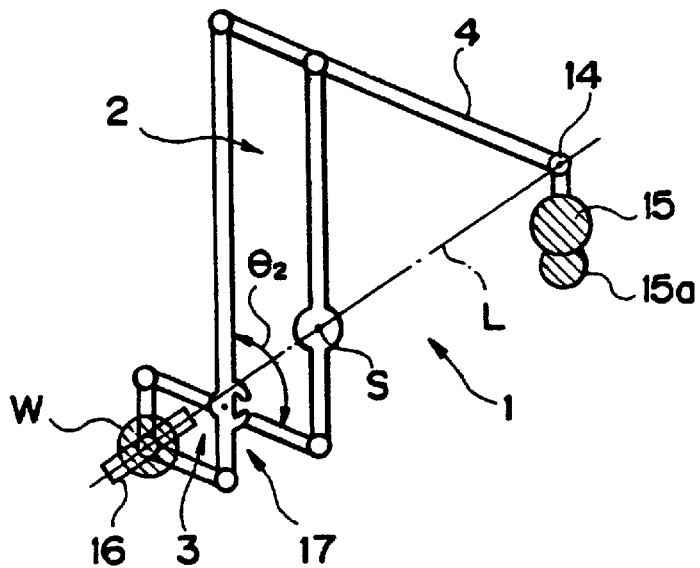
FIG. 3 is a schematic view corresponding to FIG. 1, showing a case in which an operation microscope is heavier than a counterweight.

By contrast, when the counterweight W and the operation microscope 15 are out of balance, for example, when an operation microscope 15' is lighter than the counterweight W as shown in FIG. 2, the operation microscope 15' springs upward to a large degree as soon as the unillustrated electromagnetic clutches are disengaged to unlock the parallel link mechanism 1, and the angle $\theta_1$ between the vertical arm 5b and the horizontal arm 6b becomes smaller. When an attachment 15a is attached to the operation microscope 15 as shown in FIG. 3, and thus the total weight of the operation microscope 15 and the attachment 15a becomes heavier than the counterweight W, the operation microscope 15 and the attachment 15a move downward to a large degree, and the angle $\theta_2$ between the vertical arm 5b and the horizontal arm 6b becomes larger. Accordingly, at the stage of setting the stand apparatus in a predetermined position and adjusting the balance of the parallel link mechanism 1, if the position of the counterweight W is not accurately adjusted, the parallel link mechanism 1 may move to a large degree as soon as a worker releases the parallel link mechanism 1 (as soon as the electromagnetic clutches are disengaged). This involves the danger that the parallel link mechanism 1 hits a person present nearby.

Thus, according to the present invention, a balance-sensing mechanism 17 is provided on a connection shaft 10 serving as a connection point between the first parallel link 2 and the second parallel link 3. The balance-sensing mechanism 17 and the drive mechanism 16 are operated in an interlocking manner so as to prevent a large movement of the parallel link mechanism 1 which would otherwise be induced by weight imbalance and to automatically adjust balance through the transmission of a relevant signal to the drive mechanism 16.

Figure 4:
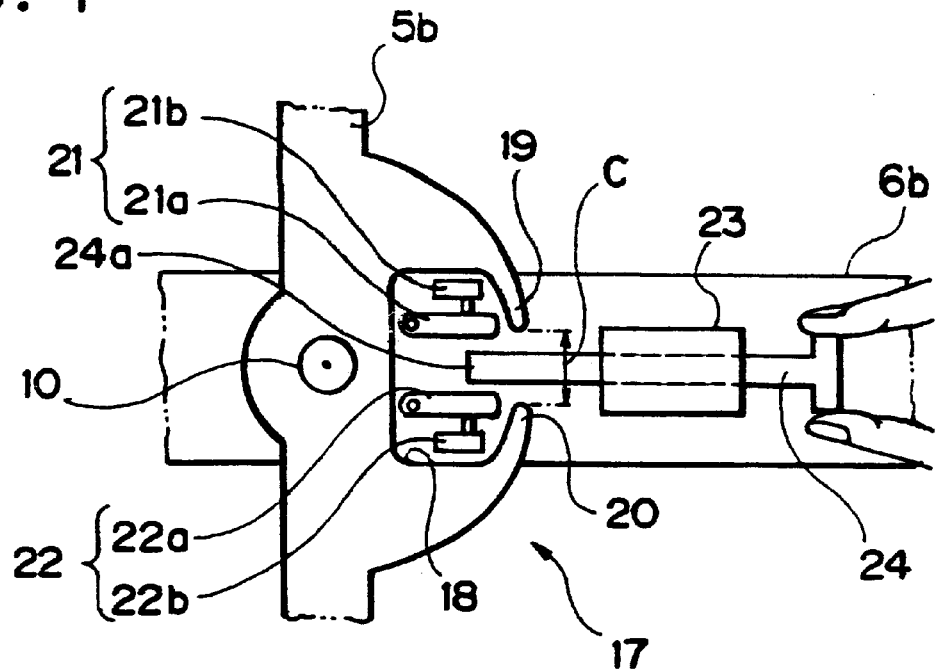
FIG. 4 is a side view showing a balance-sensing mechanism.
Figure 5:
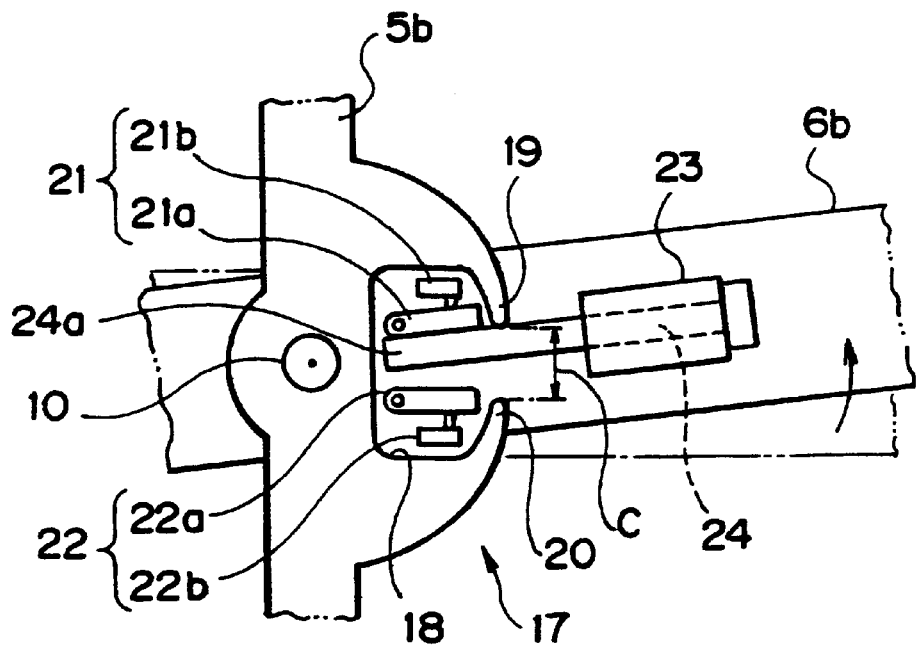
FIG. 5 is a side view corresponding to FIG. 4, showing a state in which a switch is activated.
Figure 6:
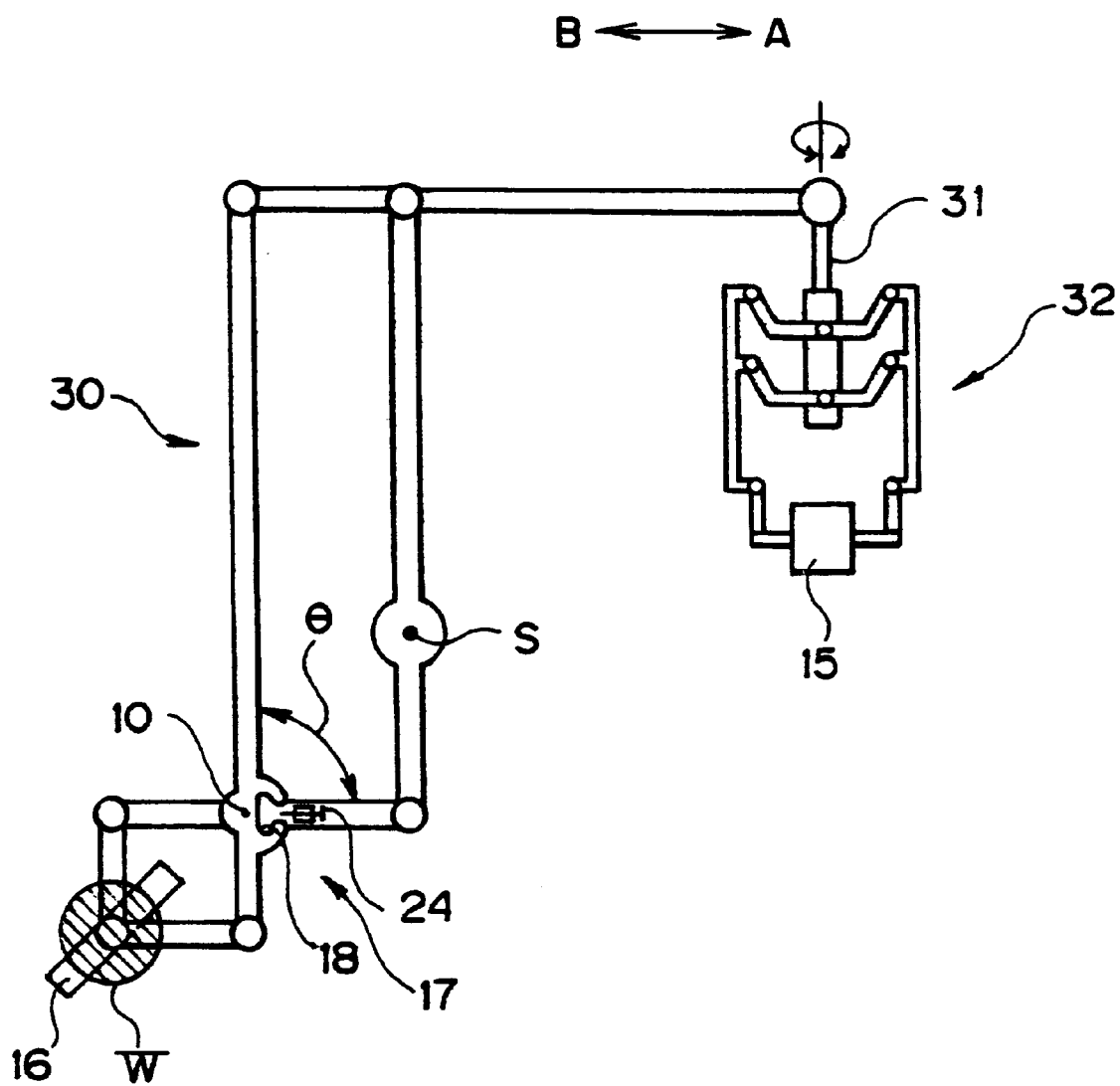
FIG. 6 is a side view showing a stand apparatus according to another embodiment of the present invention, wherein an operation microscope is supported at a tip of the stand aparatus via a balancing support mechanism.

The structure of the balance-sensing mechanism 17 will be described with reference to FIGS. 4 and 5. A hollow portion 18 is formed in the vertical arm 5b serving as "one of the intersecting arms" in a position corresponding to the connection shaft 10. The hollow portion 18 is open to the exterior of the hollow portion 18 through a predetermined clearance C. A pair of stopper portions 19 and 20 are formed at both sides of the clearance C in such a manner as to face each other. Switches 21 and 22 are provided within the hollow portion 18 in upper and lower positions, respectively. The switch 21 includes a turnable lever 21a and a switch body 21b, whereas the switch 22 includes a turnable lever 22a and a switch body 22b. When the switch 21 or 22 is activated, the activated switch 21 or 22 sends a signal to the drive mechanism 16 so as to move the counterweight W in a balancing direction corresponding to the activated switch 21 or 22.

A holder portion 23 is integrally formed on the horizontal arm 6b serving as "the other arm." A lock pin 24 is slidably provided in the holder portion 23. When the lock pin 24 is pressed forward through the holder portion 23, a tip portion 24a of the lock pin 24 is inserted through the clearance C into the hollow portion 18 and positioned between the switches 21 and 22. When the lock pin 24 is retracted, the tip portion 24a is removed from the clearance C.

Next will be described the balancing-adjustment procedure using the balance-sensing mechanism 17. In the initial state in which the stand apparatus is set in a predetermined position, the parallel link mechanism 1 is locked by means of the unillustrated electromagnetic clutches as shown in FIG. 1. While the parallel link mechanism 1 is locked, the tip portion 24a of the lock pin 24 is inserted through the clearance C and positioned between the switches 21 and 22.

Subsequently, the operation microscope 15' required for operation is attached to the tip 14 of the support arm 4. In this description, the operation microscope 15' is assumed to be lighter than the counterweight W. After the operation microscope 15' is attached, the electromagnetic clutches are energized to unlock the parallel link mechanism 1 to thereby bring the entire parallel link mechanism 1 in the free state. Since the operation microscope 15' is lighter than the counterweight W, the operation microscope 15' attempts to spring upward as shown in FIG. 2. However, since the tip portion 24a of the lock pin 24 is inserted into the clearance A, the tip portion 24a abuts the upper stopper portion 19, thereby preventing the parallel link mechanism 1 from moving to a large degree. Accordingly, there is not involved the danger that a person present near the stand apparatus is hit by part of the parallel link mechanism 1. Also, the prevention of a large movement of the parallel link mechanism 1 protects the parallel link mechanism 1 itself.

As soon as the stopper portion 19 and the lock pin 24 abut each other, the tip portion 24a of the lock pin 24 extending into the hollow portion 18 presses the upper turnable lever 21a, which, in turn, presses the switch body 22a. As a result, the switch body 22a sends a signal to the drive mechanism 16, so that the drive mechanism 16 causes the counterweight W to move in a balancing direction (toward the swing pivot S). When the movement of the counterweight W is completed to counterbalance the counterweight W and the operation microscope 15', the stopper portion 19 and the lock pin 24 are released from a strong contact Thus, the lock pin 24 can be readily removed from the clearance C.

Even though the lock pin 24 is removed, the parallel link mechanism 1 remains substantially stationary, since the parallel link mechanism 1 is already in the balanced state. Accordingly, an operator can freely move the operation microscope 15' to a desired position. When the operation microscope 15' is moved to a certain spatial position through movement of the parallel link mechanism 1, the operation microscope 15' stands motionless in the spatial position. When the position of the operation microscope 15' is completely determined, the parallel link mechanism 1 is locked by means of the electromagnetic clutches, thereby fixing the operation microscope 15' in the position.

When the total weight of the operation microscope 15 and an attachment, if attached, is heavier than the counterweight W as shown in FIG. 3, the reverse operation of the above case is performed.

In the above description, the switches 21 and 22 and the like are provided on the side of the vertical arm 5b, and the lock pin 24 is provided on the side of the horizontal arm 6b. However, this may be reversed. Further, the balance-sensing mechanism 17 is provided on the connection shaft 10, but may be provided-on another connection shaft, for example, on the connection shaft 9.

As described above, according to the present embodiment, since balancing adjustment can be automatically performed, time required for the adjustment is reduced, and a person unfamiliar with the balancing-adjustment work can readily carry out the work. Also, while the tip portion 24a of the lock pin 24 is inserted into the clearance C, even when the arms 5a and 6a of the parallel link mechanism 1 attempt to turn to a large degree, the stopper portion 19 or 20 abuts the tip portion 24a of the lock pin 24 to prevent a further turning movement of the arms 5a and 6a. Accordingly, the present embodiment does not involve the danger that the parallel link mechanism 1 moves to a large degree and may hit a person present nearby, thus providing an excellent degree of safety.

Next, another embodiment of the present invention will be described with reference to FIGS. 6 to 11.

First, the basic mechanism of the present embodiment will be described with reference to FIGS. 6 to 9. Reference numeral 30 denotes a stand apparatus utilizing a parallel link. The stand apparatus 30 is supported at a swing pivot S by an unillustrated mount. Through the deformation of the parallel link, the stand apparatus 30 can move a head link 31 vertically and horizontally. Through use of an unillustrated sub-link mechanism, the head link 31 is always held vertical in any position to which the head link 31 is moved.

An operation microscope 15 is supported by the head link 31 via a balancing support mechanism 32 according to the present embodiment. A movable counterweight W is provided on the stand apparatus 30 in a position opposite to the head link 31.

A balance-sensing mechanism 17 similar to the counterpart of the preceding embodiment is provided on one of arms intersecting on the connection shaft 10 of the stand apparatus 30. When either switch provided within a hollow portion 18 is pressed by a lock pin 24, the pressed switch indicates which is heavier, the weight of the counterweight W or the total weight of the balancing support mechanism 32 and the operation microscope 15. A drive mechanism 16 causes the counterweight W to move in such a direction as to correct the weight imbalance, thereby counterbalancing the counterweight W and a combined assembly of the balancing support mechanism 32 and the operation microscope 15.

While the stand apparatus 30 is in the balanced state described above, since the lock pin 24 is not in contact with either of the upper and lower switches as mentioned previously, the lock pin 24 can be removed from the hollow portion 18 so as to allow the stand apparatus 30 to be used. Once the stand apparatus 30 is brought in the balanced state, the balanced state is maintained in any spatial position to which the operation microscope 15 is moved. Accordingly, the operation microscope 15 can stand motionless in a desired spatial position.

Figure 7:
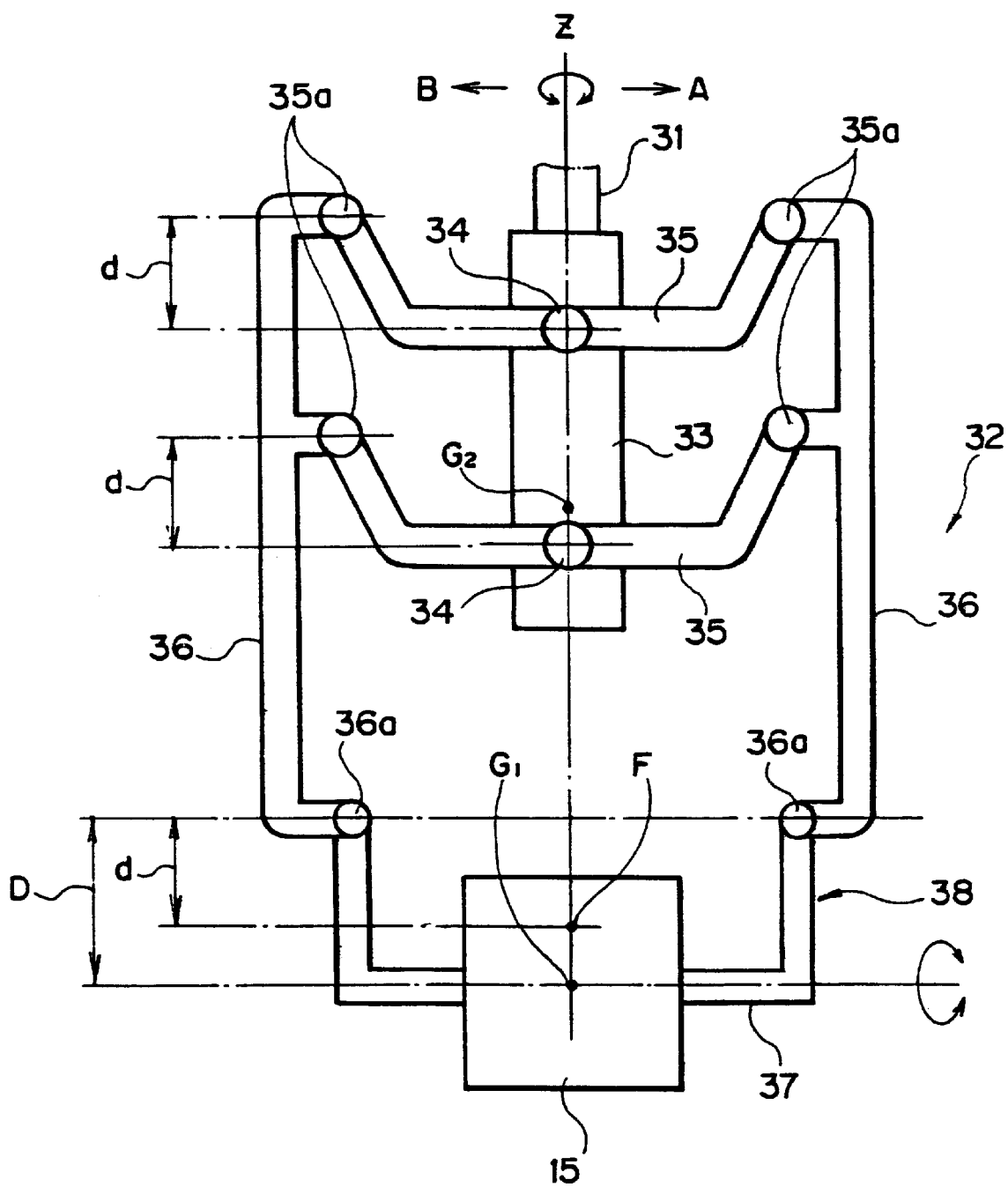
FIG. 7 is a side view showing a normal state of the balancing support mechanism.

Next will be described the balancing support mechanism 32 for supporting the operation microscope 15. In FIG. 7, symbol A denotes the front side, symbol B denotes the rear side, and a direction perpendicular to the plane of the present drawing sheet is the right-left direction.

A center member 33 rotatable about a vertical axis Z is provided at the lower portion of the head link 31. Shaft supports 34 are provided on the center member 33 in upper and lower positions. Horizontal links 35 are supported by the corresponding shaft supports 34 and extend in the front-rear direction. Both end portions 35a of the horizontal links 35 are bent upward, so that the shaft support 34 is located below both end portions 35a in an amount of d.

The upper and lower shaft supports 34 of the center member 33 not only support the horizontal links 35 in a turnable manner but also allow the horizontal links 35 to slide in their longitudinal direction by the same length.

A pair of parallel vertical links 36 are supported by the horizontal links 35 such that one vertical link 36 is attached in a turnable manner to the end portions of the upper and lower horizontal links 35 on one side of the horizontal links 35 and the other vertical link 36 is attached in the same manner on the other side of the horizontal links 35. The vertical links 36 extend downward and have lower end portions 36a. A support link 38 having a shape of a squarish letter U as a whole is attached in a turnable manner to the lower end portions 36a. The support link 38 includes a tilt shaft 37, which corresponds to the bottom side of the squarish letter U. Since the support point of the horizontal link 35 is located below the both end portions 35a in an amount of d, a stationary point F, which stands stationary when the end portions 35a of the horizontal links 35 move vertically, is located below the lower end portions 36a in an amount of d on the vertical axis Z. The tilt shaft 37 of the support link 38 is located below the stationary point F in an amount of d. That is, the distance D between the lower end portions 36a and the tilt shaft 37 is greater than the distance d between the lower end portions 36a and the stationary point F (D>d). The operation microscope 15 is attached to the tilt shaft 37 in a manner tiltable in the right-left direction.

Figure 8:
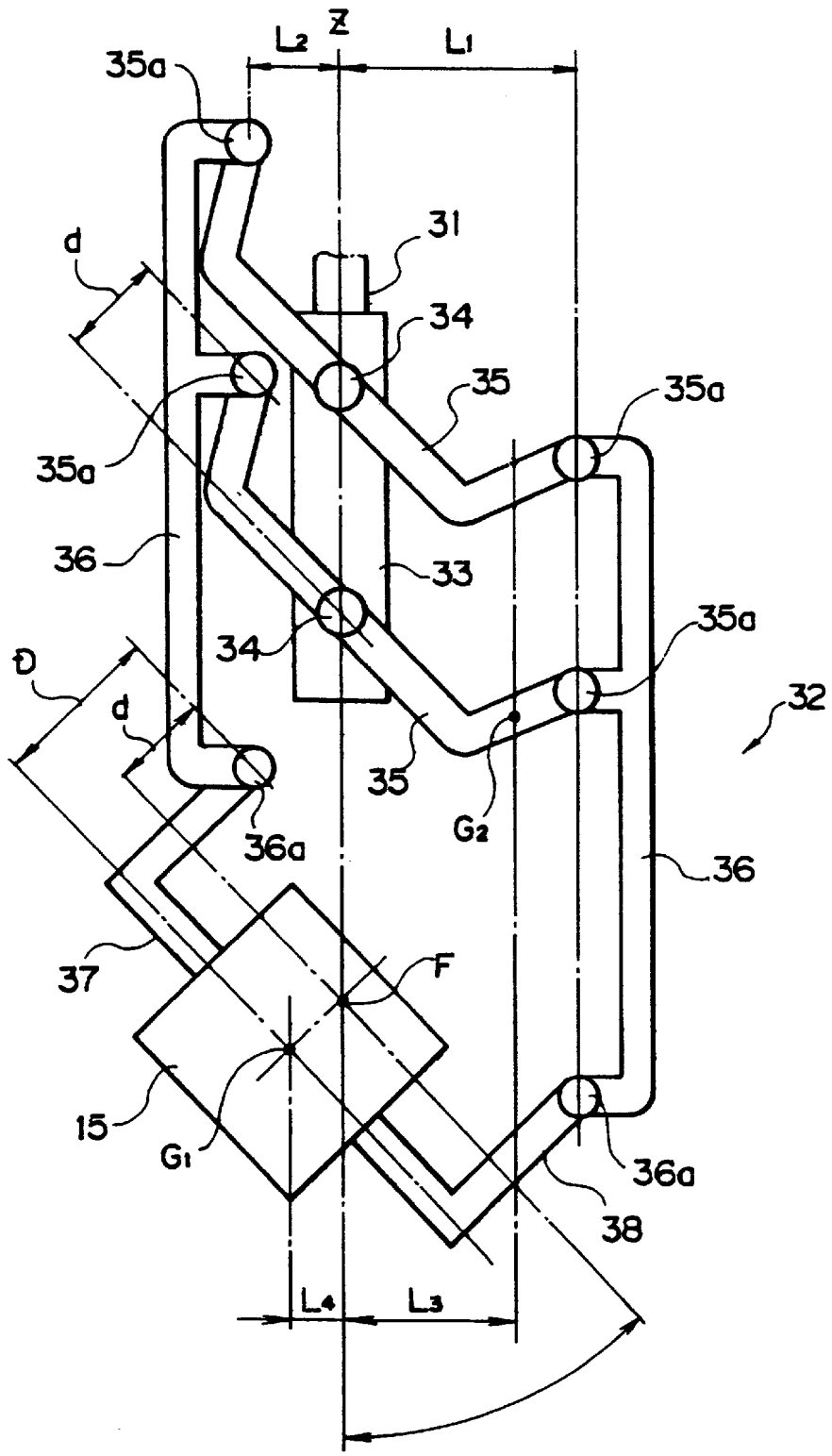
FIG. 8 is a side view showing an inclined state of the balancing support mechanism.

In the state of FIG. 7, the combined center $G_1$ of gravity of the operation microscope 15 and the support link 38 is located on the vertical axis Z; thus, the weight balance is kept in the front-rear direction with respect to the vertical axis Z. When the end portions 35a of the horizontal links 35 are inclined to either side as shown in FIG. 8, distance $L_1$ from the vertical axis Z to the end portions 35a on one side becomes different to distance $L_2$ from the vertical axis Z to the end portions 35a on the other side, since the shaft supports 34 are located below the corresponding end portions 35a. Also, the combined center $G_2$ of gravity of the horizontal links 35 and the vertical links 36 shifts from the vertical axis Z to one side in an amount of $L_3$.

At the same time, the combined center $G_1$ of gravity of the operation microscope 15 and the support link 38 shifts to the side opposite to the center $G_2$ of gravity in an amount of $L_4$. The both centers $G_1$ and $G_2$ of gravity balance each other with respect to the center member 33. That is, because of $G_1 \times L_4 = G_2 \times L_3$, the balancing support mechanism 32 is sustained in the inclined state.

Figure 9:
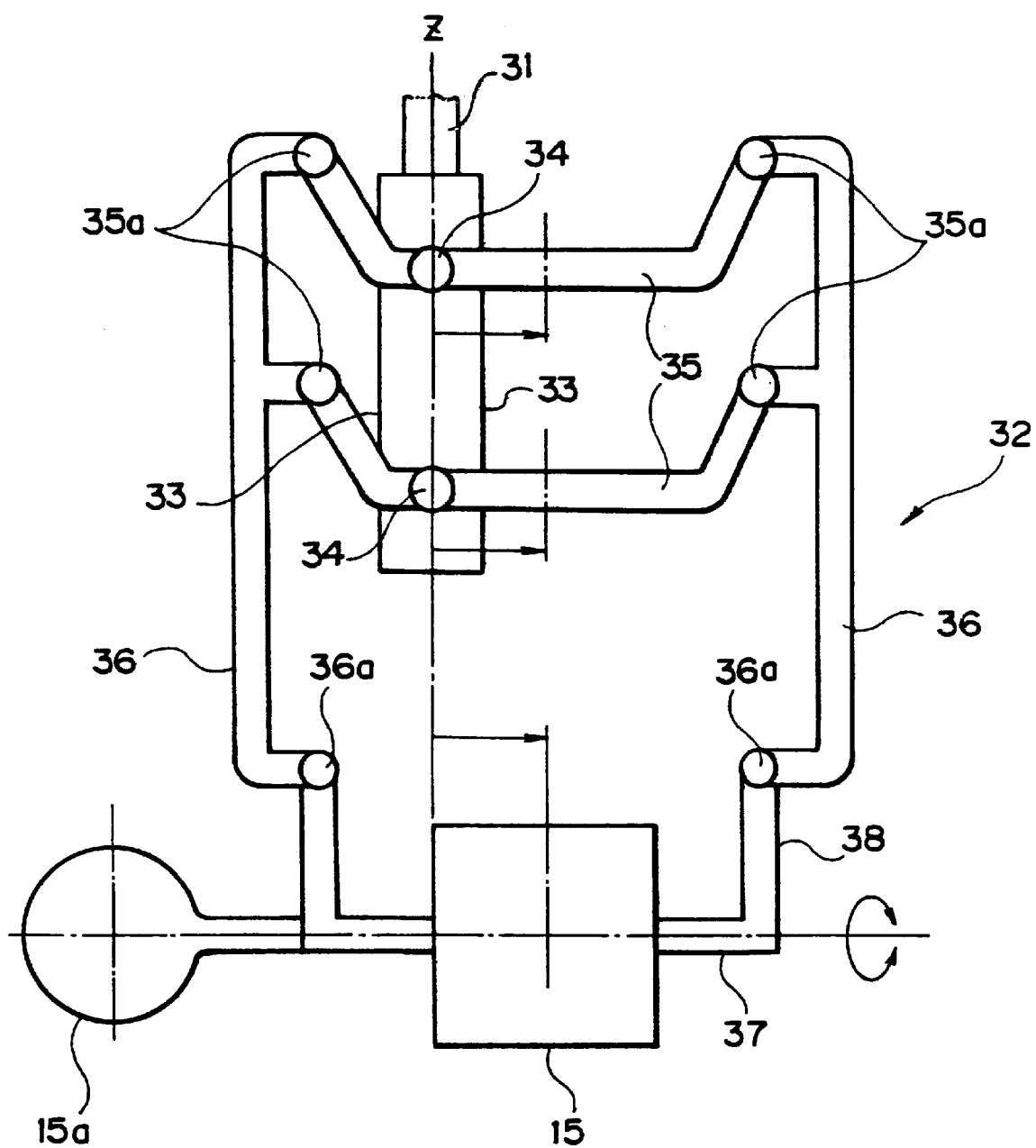
FIG. 9 is a side view of the balancing support mechanism, showing a state in which horizontal links are slid.

Also, as shown in FIG. 9, when the combined center $G_1$, of gravity of the microscope 15 and the support link 38 shifts due to addition of the attachment 15a to either side of the operation microscope 15, the horizontal links 35 slide on the shaft supports 34 in a balancing direction. Once the balance is kept, the balancing support mechanism 32, even when inclined as shown in FIG. 8, is sustained in the balanced state.

According to the present embodiment, the microscope 15 is supported by the support link 38 which is attached in a turnable manner to the lower end portions 36a of the vertical links 36. Accordingly, the vertical links 36 are not present around the operation microscope 15, whereby a sufficient amount of space can be secured around the operation microscope 15.

Figure 10:
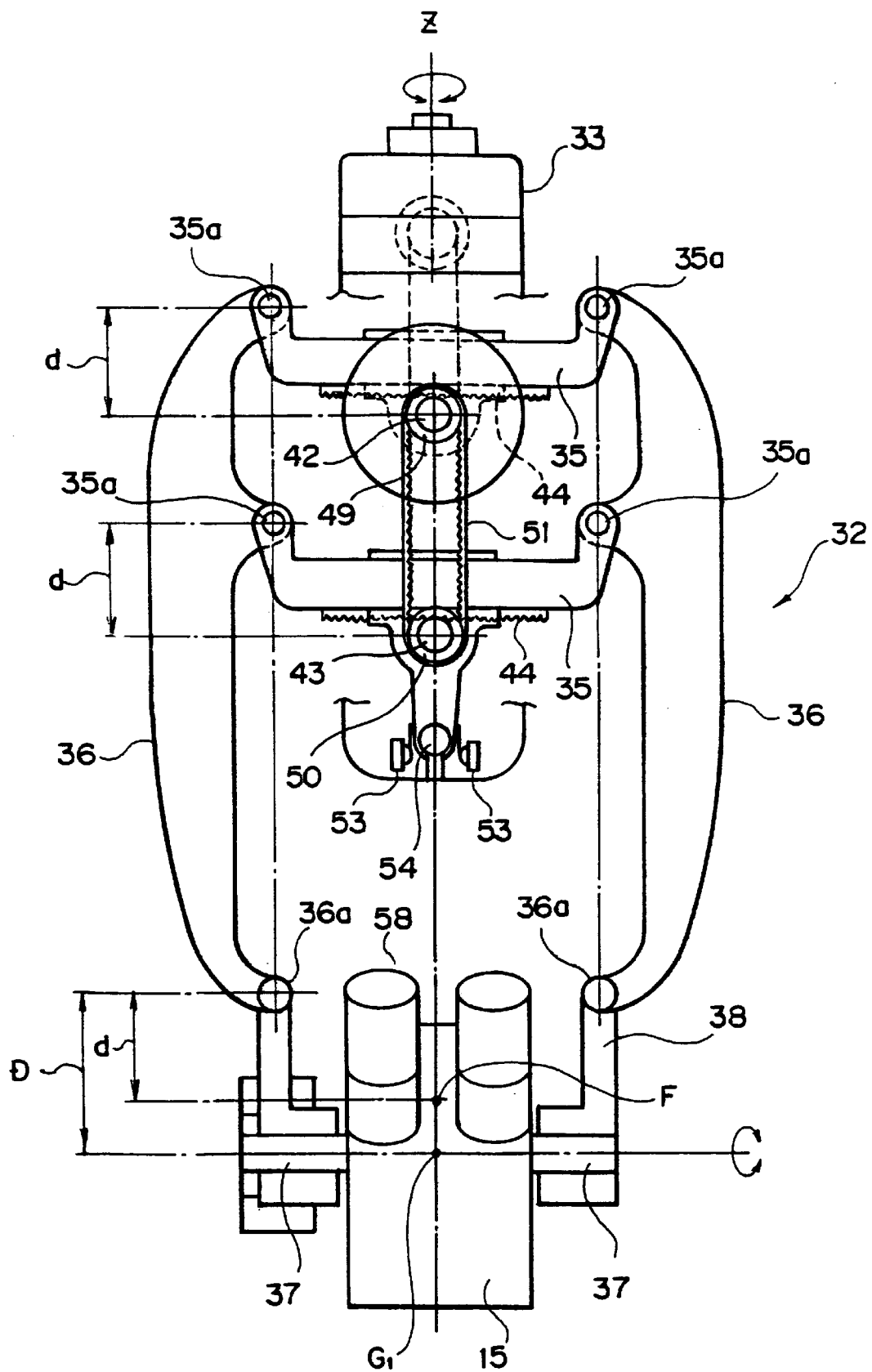
FIG. 10 is a partially-sectioned side view showing a specific structure of the balancing support mechanism as viewed from a main doctor side.
Figure 11:
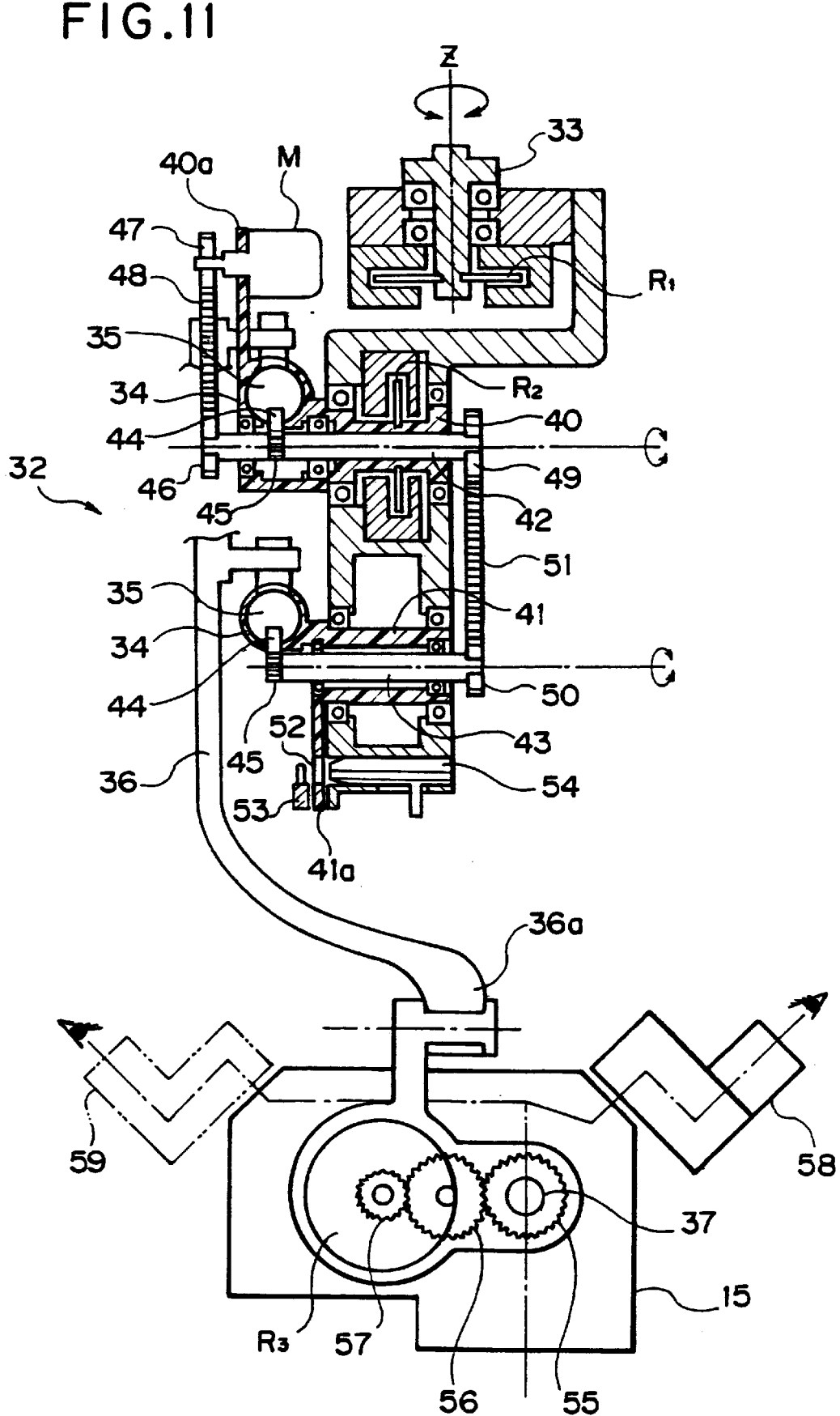
FIG. 11 is a sectional view showing a specific structure of the balancing support mechanism.

Next, the specific structure of the balancing support mechanism 32 will be described with reference to FIGS. 10 and 11. The same features as those of FIGS. 6 to 9 appearing in the above description of mechanisms are denoted by common reference numerals, and redundant description is omitted.

The frame-like center member 33 is attached to the head link 31 of the stand apparatus 30 via bearings (illustrated, but not denoted by a reference numeral) such that the center member 33 is rotatable about the vertical axis Z. An electromagnetic clutch $R_1$ is provided between the head link 31 and the center member 33 so as to lock the center member 33 in a certain rotational position about the vertical axis Z.

Shafts 42 and 43 covered with outer tubes 40 and 41, respectively, are provided in the upper and lower positions of the center member 33 such that they penetrate the center member 33. Bearings are interposed between the center member 33 and each of the outer tubes 40 and 41, between the outer tube 40 and the shaft 42, and between the outer tube 41 and the shaft 43. The horizontal link 35 slidably penetrates one end of each of the outer tubes 40 and 41. Rack gears 44 formed on the bottom surfaces of the horizontal links 35 are engaged with pinion gears 45 formed on the shafts 42 and 43.

An electromagnetic clutch $R_2$ is provided between the upper outer tube 40 and the center member 33 so as to lock the outer tube 40 in a certain rotational position. A motor M is mounted on an upwardly facing flange 40a which is formed at one end of the outer tube 40. A timing belt 48 is looped around and mounted on a gear 46 provided at one end of the shaft 42 and a gear 47 provided on the rotational shaft of the motor M. A gear 49 is attached to the other end of the shaft 42, and a gear 50 is attached to the other end of the shaft 43. A timing belt 51 is looped around and mounted on the gears 49 and 50. The motor M, the shafts 42 and 43, the gears 46, 49, and 50, the rack gears 44, the pinion gears 45, the timing belts 48 and 51, and the like constitute the "slide mechanism" of the present invention.

A downwardly facing flange 41a is formed at one end of the lower outer tube 41. A laterally elongated opening 52 is formed in the flange 41a. Switches 53 are provided on both front and rear sides of the opening 52. A pin 54 is provided at the lower end of the center member 33 in a manner protrudable into the opening 52. The pin 54, when protruded into the opening 52, presses the switch 53 to cause the motor M to rotate. The rotational direction of the motor M depends on which of the switches 53 is pressed. The switches 53, the pin 54, and the like constitute the "imbalance sensor" of the present invention.

The vertical links 36 are attached in a turnable manner to both end portions 35a of the horizontal links 35. The support link 38 is attached in a turnable manner to the lower end portions 36a of the vertical links 36. An operation microscope 15 is attached in a tiltable manner to the tilt shaft 37 of the support link 38. The tilt shaft 37 also serves as an optical outlet for the operation microscope 15. An unillustrated "attachment," such as a video camera or a side viewer, can be connected to the tilt shaft 37, as needed. The tilt shaft 37 is connected to an electromagnetic clutch $R_3$ via gears 55, 56, and 57 so as to lock the operation microscope 15 in a certain rotational position about the tilt shaft 37.

The operation microscope 15 has an eyepiece section 58 for main doctor use and an eyepiece section 59 for assistant doctor use. Since the vertical links 36 are not present around the operation microscope 15, there is no hindrance to observation through the eyepiece sections 58 and 59.

When an attachment (for example, a video camera) is to be attached to either end of the tilt shaft 37, the pin 54 is held protruded into the opening 52. Through the establishment of this state, even when a weight imbalance occurs due to the addition of an attachment, the pin 54 abuts both end portions of the opening 52 and serves as a stopper. Accordingly, the horizontal links 35 do not incline to a large degree.

At the same time, the pin 54 presses either one of the switches 53 located on both sides of the opening 52. As a result, a signal generated from the pressed switch 53 causes the motor M to rotate accordingly. The rotational force of the motor M is transmitted to the upper and lower shafts 42 and 43 in the same manner via the timing belts 48 and 51, respectively. Thus, through the engagement between the pinion gears 45 and the rack gears 44, the horizontal links 35 slide synchronously over the same length in a balancing direction.

When a weight balance is thus kept, the pin 54 is located in the neutral position between the switches 53 and thus do not press either of the switches 53. Accordingly, the motor M stops rotating. After the motor M is completely stopped, the pin 54 is removed from the opening 52. This enables a user to incline the horizontal links 35 in a desired direction for convenience of observation. Even when the horizontal links 35 are inclined, the combined center $G_1$, of gravity of the operation microscope 15 and the support link 38 balances with the combined center $G_2$ of gravity of the horizontal links 35 and the vertical links 36.

In the above description, means for locking components in certain rotational positions are the electromagnetic clutches $R_1$ to $R_3$. However, air locks (pneumatic locking means) may replace the electronic clutches $R_1$ to $R_3$.

What is claimed is:

1. A medical stand apparatus, comprising:
    a parallel link mechanism including arms, the parallel link mechanism being held at a predetermined swing pivot;
    at least one of a medical optical device and an attachment sustained at one end of the parallel link mechanism;
    a counterweight provided at another end of the parallel link mechanism so as to counterbalance with said at least one of the medical optical device and the attachments;
    a drive mechanism for moving the counterweight in a balancing direction;
    a connection shaft on which the arms of the parallel link mechanism intersect with each other; and
    a balance-sensing mechanism for sensing a balancing state of the parallel link mechanism and for sending a signal to the drive mechanism, said balance-sensing mechanism being disposed on the connection shaft,
    wherein said balance-sensing mechanism comprises a pair of stopper portions formed on one of the intersecting arms at a position corresponding to the connection shaft in such a manner as to face each other with a predetermined clearance formed between the stopper portions; a lock pin provided on the other arm such that a tip portion of the lock pin can be inserted into or removed from the clearance; and a pair of switches provided on the one arm such that a relevant switch is pressed by the tip portion of the lock pin when the angle between the arm is displaced.

2. A medical stand apparatus according to claim 1, wherein each of said pair of switches comprises a switch body which generates a signal, and a turnable lever which is pressed toward the switch body by the tip portion of the lock pin.

3. A medical stand apparatus according to claim 1, wherein:
    the arms include parallel vertical and horizontal arms and a support arm; and
    the parallel link mechanism comprises a first parallel link including ones of said parallel vertical and horizontal arms, a second parallel link including remaining ones of said parallel vertical and horizontal arms, and the support arm is formed by extending one end of an upper one of said horizontal arms of the first parallel link, said at least one of the medical optical device and the attachment being supported at a tip of the support arm, the counterweight being provided on a part of the second parallel link via said drive mechanism.

4. A balancing support mechanism for a medical optical device to be supported at a tip of a stand apparatus, comprising:
    a center member supported at the tip of the stand apparatus in a manner rotatable about a vertical axis;
    a pair of parallel horizontal links which are supported in a turnable manner at upper and lower positions of said center member such that each horizontal link is supported at a position located lower than both end portions of the horizontal link;

a pair of vertical links, each of which is supported in a turnable manner by said horizontal links at the corresponding upper and lower end portions of the horizontal links; and a support link which is supported in a turnable manner at the lower end portions of said vertical links and extend between said vertical links in parallel with said horizontal links and which has a tilt shaft for supporting the medical optical device, wherein the tilt shaft is located below a stationary point which stands stationary even when both end portions of said horizontal links move vertically; and the medical optical device being mountable to the tilt shaft of the support link, a combined center of gravity of the medical optical device and said support link when the medical optical device is mounted counterbalances with the combined center of gravity of said horizontal links and said vertical links in the direction in which said vertical links face each other with respect to the vertical axis.

5. A balancing support mechanism for a medical optical device according to claim 4, wherein said upper and lower horizontal links slide synchronously by the same length in the longitudinal direction of the horizontal links with respect to said center member.

6. A balancing support mechanism for a medical optical device according to claim 5, further comprising an imbalance sensor for sensing an imbalanced state between the combined center of gravity of the medical optical device and said support link and the combined center of gravity of said horizontal links and said vertical links, and a slide mechanism for synchronously sliding said upper and lower horizontal links to such positions in accordance with a signal from said imbalance sensor that balance is kept.

\* \* \* \* \*